US012687549B2

(12) United States Patent
Kaur et al.

(10) Patent No.: US 12,687,549 B2
(45) Date of Patent: Jul. 21, 2026

(54) MULTIPLEXED TOTAL ANTIBODY AND ANTIBODY-CONJUGATED DRUG QUANTIFICATION ASSAY

(71) Applicant: Genentech, Inc., South San Francisco, CA (US)

(72) Inventors: Surinder Kaur, Lafayette, CA (US); Ola Saad, Walnut Creek, CA (US); Manjui Violet Lee, Redwood City, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 18/370,295

(22) Filed: Sep. 19, 2023

(65) Prior Publication Data

US 2024/0012003 A1     Jan. 11, 2024

Related U.S. Application Data

(63) Continuation of application No. 16/883,348, filed on May 26, 2020, now abandoned, which is a continuation of application No. 15/468,323, filed on Mar. 24, 2017, now abandoned.

(60) Provisional application No. 62/313,608, filed on Mar. 25, 2016.

(51) Int. Cl.
*G01N 33/68* (2006.01)
*G01N 33/94* (2006.01)

(52) U.S. Cl.
CPC ..... *G01N 33/6857* (2013.01); *G01N 33/6848* (2013.01); *G01N 33/6854* (2013.01); *G01N 33/94* (2013.01); *G01N 2560/00* (2013.01)

(58) Field of Classification Search
CPC ........... G01N 2560/00; G01N 33/6848; G01N 33/6854; G01N 33/6857; G01N 33/94; G01N 1/4044; G06Q 10/06; G06Q 10/0631; G06Q 10/0633; G06Q 50/04; G06Q 50/10
See application file for complete search history.

(56) References Cited

U.S. PATENT DOCUMENTS

| | | | |
|---|---|---|---|
| 7,521,541 B2 | 4/2009 | Eigenbrot et al. | |
| 7,666,582 B2 | 2/2010 | Pawel-Rammingen et al. | |
| 7,723,485 B2 | 5/2010 | Junutula et al. | |
| 8,541,178 B2 | 9/2013 | Kaur et al. | |
| 8,679,767 B2 | 3/2014 | Kaur et al. | |
| 11,860,156 B2 * | 1/2024 | Darwish | G01N 33/6857 |
| 2009/0286258 A1 | 11/2009 | Kaur et al. | |
| 2010/0015652 A1 | 1/2010 | Granda et al. | |
| 2012/0315645 A1 | 12/2012 | Kaur et al. | |
| 2015/0316515 A1 | 11/2015 | Lauber et al. | |
| 2017/0315132 A1 | 11/2017 | Kaur et al. | |
| 2017/0370906 A1 | 12/2017 | Darwish et al. | |
| 2021/0123928 A1 | 4/2021 | Kaur et al. | |

FOREIGN PATENT DOCUMENTS

| | | |
|---|---|---|
| EP | 1740954 B1 | 8/2015 |
| WO | 2005101017 A1 | 10/2005 |
| WO | 2009080278 A1 | 7/2009 |
| WO | 2010002911 A2 | 1/2010 |
| WO | 2010009124 A2 | 1/2010 |
| WO | 2011042027 A2 | 4/2011 |
| WO | 2011159878 A1 | 12/2011 |
| WO | 2012074757 A1 | 6/2012 |
| WO | 2012155019 A1 | 11/2012 |
| WO | 2013064684 A1 | 5/2013 |
| WO | 2014078374 A2 | 5/2014 |
| WO | 2014177615 A2 | 11/2014 |
| WO | 2015040125 A1 | 3/2015 |

OTHER PUBLICATIONS

Adamo et al., "Drug-to-antibody determination for an antibody-drug-conjugate utilizing cathepsin B digestion coupled with reversed-phase high-pressure liquid chromatography analysis," J. Chromatogr. A, 2017, Jan. 20; 1481, pp. 44-52; Epub Dec. 19, 2016.*
Anderson, L , et al., "Quantitative mass spectrometric multiple reaction monitoring assays for major plasma proteins", Molecular & Cellular Proteomics 5, 573-588 (2006).
Boushaba, R , et al., "Kinetics of whole serum and prepurified IgG digestion by pepsin for F(ab')2 manufacture", Biotechnol Prog 19, 1176-1182 (2003).
Carr, S , et al., "Protein quantitation through targeted mass spectrometry: the way out of biomarker purgatory?", Clinical Chemistry 54(11), 1749-1752 (2008).
Chen, T , et al., "Chemical de-conjugation for investigating the stability of small molecule drugs in antibody-drug conjugates", Journal of Pharmaceutical and Biomedical Analysis 117, 304-310 (2016).
Chen, J , et al., "Development of a Native Nanoelectrospray Mass Spectrometry Method for Determination of the Drug-to-Antibody Ratio of Antibody-Drug Conjugates", Anal Chem 85(3), 1699-1704 (2013).
Dere, R , et al., "PK assays for antibody-drug conjugates: case study with ado-trastuzumab emtansine", Bioanalysis 5 (9), 1025-1040 (2013).
Farias, S , et al., "Mass Spectrometric Characterization of Transglutaminase Based Site-Specific Antibody-Drug Conjugates", Bioconjugate Chem 25(2), 240-250 (2014).

(Continued)

*Primary Examiner* — Gregory S Emch

(74) *Attorney, Agent, or Firm* — Viksnins Harris Padys Malen LLP

(57) ABSTRACT

Methods are disclosed to detect, characterize, measure, and quantify human and humanized antibodies, and their conjugates, that may be present in pre-clinical animal biological samples, or human biological samples, including plasma/serum and tissue samples.

16 Claims, 5 Drawing Sheets

(56)                    References Cited

OTHER PUBLICATIONS goldbio.com , Printout retrieved from https://www.goldbio.com/articles/article/reducing-agents-part-2-of-4-l-glutathione, 5 pages, on Sep. 30, 2019.

Gong, C , et al., "Post-pellet-digestion precipitation and solid phase extraction: A practical and efficient workflow to extract surrogate peptides for ultra-high performance liquid chromatography—tandem mass spectrometry bioanalysis of a therapeutic antibody in the low n", Journal of Chromatography 1424, 27-36 (2015).

Hagman, C , et al., "Absolute quantification of monoclonal antibodies in biofluids by liquid chromatography-tandem mass spectrometry", Anal Chem 80, 1290-1296 (2008).

He, J , et al., "High-Resolution Accurate-Mass Mass Spectrometry Enabling In-Depth Characterization of in Vivo Biotransformations for Intact Antibody-Drug Conjugates", Anal Chem 89, 5476-5483 (2017).

Heudi, O , et al., "Towards absolute quantification of therapeutic monoclonal antibody in serum by LC-MS/MS using isotope-labeled antibody standard and protein cleavage isotope dilution mass spectrometry", Anal Chem 80, 4200-4207 (2008).

Janin-Bussat, M , et al., "Characterization of antibody drug conjugate positional isomers at cysteine residues by peptide mapping LC-MS analysis", Journal of Chromatography B 981-982, 9-13 (2015).

Ji, C , et al., "A universal strategy for development of a method for absolute quantification of therapeutic monoclonal antibodies in biological matrices using differential dimethyl labeling coupled with ultra performance liquid chromatography-tandem mass spectrometry", Anal Chem 81, 9321-9328 (2009).

Jiang, H , et al., "Innovative Use of LC-MS/MS for Simultaneous Quantitation of Neutralizing Antibody, Residual Drug, and Human Immunoglobulin G in Immunogenicity Assay Development", Anal Chem 86(5), 2673-2680 (2014).

Jones, R , et al., "A protocol for 'enhanced pepsin digestion': a step by step method for obtaining pure antibody fragments in high yield from serum", Journal of Immunological Methods 275, 239-250 (2003).

Junutula, J , et al., "Rapid identification of reactive cysteine residues for site-specific labeling of antibody-Fabs", Journal of Immunological Methods 332, 41-52 (2008).

Junutula, J , et al., "Site-specific conjugation of a cytotoxic drug to an antibody improves the therapeutic index", Nature Biotechnology 26(8), 925-932 (2008).

Kaur, S , "ADC Analyte Diversity and Appropriate PK Assays Part 1: Background & Bioanalytical Strategy", European Bioanalysis Forum—ADC Training Day, 35 pages, Jun. 20, 2017.

Kaur, S , et al., "Bioanalytical assay strategies for the development of antibody-drug conjugate biotherapeutics", Bioanalysis 5(2), 201-226 (2013).

Kleemann, G , et al., "Characterization of IgG1 Immunoglobulins and Peptide-Fc Fusion Proteins by Limited Proteolysis in Conjunction with LC-MS", Anal Chem 80, 2001-2009 (2008).

Kuhn , "Developing multiplexed assays for troponin I and interleukin-33 in plasma by peptide immunoaffinity enrichment and targeted mass spectrometry", Clinical Chemistry 55(6), 1108-1117 (2009).

Li, Y , et al., "An enzymatic deconjugation method for the analysis of small molecule active drugs on antibody-drug conjugates", MAbs 8(4), 698-705 (2016).

Liu, H , et al., "Quantitation of a recombinant monoclonal antibody in monkey serum by liquid chromatography-mass spectrometry", Analytical Biochemistry 414, 147-153 (2011).

Nassur, S , et al., "Structural characterization of antibody drug conjugate by a combination of intact, middle-up and bottom-up techniques using sheathless capillary electrophoresis—Tandem mass spectrometry as nanoESI infusion platform and separation method", Analytica Chimica Acta 918, 50-59 (2016).

Patent Cooperation Treaty , International Searching Authority, Search Report and Written Opinion for PCT/US2017/023971, 10 pages, May 19, 2017.

Redman, E , et al., "Characterization of Intact Antibody Drug Conjugate Variants Using Microfluidic Capillary Electrophoresis—Mass Spectrometry", Anal Chem 88(4), 2220-2226 (2016).

sigmaaldrich.com , "Dephosphorylation Procedures for DNA and Proteins", www.sigmaaldrich.com/US/en/technical-documents/protocol/genomics/cloning-and-expression/dephosphorylation, 4 pages, accessed on Oct. 31, 2022.

Su, D , et al., "Custom-Designed Affinity Capture LC-MS F(ab')2 Assay for Biotransformation Assessment of Site-Specific Antibody Drug Conjugates", Anal Chem 88(23), 11340-11346 (2016).

ThermoFisher , http://assets.thermofisher.com/TFS-Assets/LSG/manuals/MAN0011972_Dephosphorylation_Proteins_UG.pdf, 1 page, on Mar. 11, 2019, created/modified on Internet May 2, 2013.

Wagner-Rousset, E , et al., "Antibody-drug conjugate model fast characterization by LC-MS following IdeS proteolytic digestion", mAbs 6(1), 173-184 (2014).

Wikipedia , "Protein phosphatase", https://en.wikipedia.org/wiki/Protein_phosphatase, 8 pages, accessed on Oct. 31, 2022.

Xu, K , et al., "Characterization of intact antibody-drug conjugates from plasma/serum in vivo by affinity capture capillary liquid chromatography-mass spectrometry", Analytical Biochemistry 412, 56-66 (2011).

Xu, K , et al., "Characterization of the drug-to-antibody ratio distribution for antibody-drug conjugates in plasma/serum", Bioanalysis 5(9), 1057-1071 (2013).

Hyung, et al., "Multiplexed Quantitative Analysis of Antibody—Drug Conjugates with Labile CBI-Dimer Payloads In Vivo Using Immunoaffinity LC-MS/MS", Anal Chem 94, 1158-1168 (2022).

Zhu, et al., "Current LC-MS-based strategies for characterization and quantification of antibody-drug conjugates", Journal of Pharmaceutical Analysis 10, 209-220 (2020).

* cited by examiner acDrug total Ab

IS Peak Area

Figure 3

HCl +MeOH

AmBic+MeOH

MULTIPLEXED TOTAL ANTIBODY AND ANTIBODY-CONJUGATED DRUG QUANTIFICATION ASSAY

CROSS REFERENCE TO RELATED APPLICATIONS

This continuation application claims priority to non-provisional U.S. application Ser. No. 16/883,348, filed 26 May 2020, which claims priority to non-provisional U.S. application Ser. No. 15/468,323, filed 24 Mar. 2017, which claims priority to U.S. Provisional Application No. 62/313,608, filed on 25 Mar. 2016, which are incorporated by reference in entirety.

TECHNICAL FIELD

This disclosure relates to methods of capturing, detecting, analyzing, characterizing, and quantifying antibody-drug conjugates, and their fragments and metabolites, in non-biological or biological matrices by mass spectrometry.

BACKGROUND

With the approval of brentuximab vedotin (trade name: Adcetris®) and trastuzumab emtansine (trade name: Kadcyla®, Genentech Inc.), the therapeutic potential of antibody drug conjugates (ADCs) providing targeted delivery of pharmaceutically active drug or toxin molecules to specific sites of action has been confirmed, and further research and development has resulted. ADCs are generally composed of an antibody, a pharmaceutically active small molecule drug or toxin (often referred to as the "payload"), and an optional linker to connect the two. The linker, typically a peptide derivative, joins the small-molecule, highly potent drug to the large-molecule antibody, which is selected or engineered to target the antigens on a specific cell type, typically a cancer cell. ADCs thus employ the powerful targeting ability of monoclonal antibodies to specifically deliver highly potent, conjugated small molecule therapeutics to a cancer cell.

As successful ADC candidates emerge from ongoing research and development programs and proceed to clinical evaluation and market approval, safety and efficacy assays that can effectively assess the complex chemical composition created by combination of a large protein complex (antibody) and a typically much smaller, but highly potent, drug molecule, are needed. The characterization of the drug-antibody linkage, antibody and drug concentrations, as well as the drug-to-antibody ratio, and stability of these ADC compositions must be initially established, and then monitored for consistency, as these properties of the ADC can affect the bioactivity, pharmacokinetics, distribution, immunogenicity, safety, and stability profiles of these therapeutic entities.

Liquid chromatography-tandem mass spectrometry is a powerful tool for protein analysis and quantitation in very complex matrices like plasma/serum/tissue samples. Since peptides resulting from the digestion of the protein of interest and other endogenous proteins may have the same or similar nominal mass, the second dimension of MS fragmentation often provides a unique fragment of a peptide of interest. The combination of the specific parent peptide and the unique fragment ion is used to selectively monitor for the molecule to be quantified. Such approach is termed "Multiple reaction monitoring" (MRM), also referred to as Selected Reaction Monitoring (SRM), which is a commonly used mode for protein quantification.

SUMMARY

Aspects of this disclosure provide robust methods to detect and quantify total antibody and antibody-conjugated drug quantity by digestion of the antibody and separation of the drug component of the ADC, followed by simultaneous chromatographic and mass spectrophotometric analysis of the resulting composition of the combined released drug and peptides from the digested antibody.

Thus, in certain aspects, this disclosure provides methods of quantifying both antibody-conjugated drug and total antibody concentrations of an antibody-drug conjugate. These methods include contacting an antibody-drug conjugate (ADC) with a composition that reduces the antibody to form a denatured antibody and digesting the denatured antibody to form a digested antibody-drug conjugate peptide mixture in a single analysis sample. The digested drug and peptide mixture in the single analysis sample may then be analyzed by LC-MS/MS to detect at least one signature peptide from the antibody and a drug.

In these methods, the ADC to be analyzed directly in the matrix that it may be found in, such as a buffer, whole blood, serum, plasma, cerebrospinal fluid, saliva, urine, lymph, bile, feces, sweat, vitreous, tears, or tissue before the ADC is contacted with a composition that reduces the antibody. In instances in which the ADC is found in a matrix in a concentration that is too low for sufficient analysis or is found in a biological sample that contains molecules that could interfere with efficient or accurate analysis of the ADC, the ADC may be enriched, for example, by techniques such as size exclusion chromatography, dialysis, selective precipitation, differential centrifugation, filtration, gel electrophoresis, liquid chromatography, reversed-phase chromatography, immunoprecipitation, SpinTrap™ purification columns including protein A and protein G, NHS and streptavidin iron or phosphorus or immobilized antibodies or lectin, paramagnetic beads, immuno-depletion, fractionation, solid phase extraction, phosphopeptide enrichment, polyacrylamide gel electrophoresis, or desalting. Thus, the analysis methods of this disclosure may proceed with the ADC, or fragments thereof, bound to an affinity capture media, which may include optional washing and eluting steps to further purify or enrich the ADC, or ADC fragments, to be analyzed.

These analysis methods may also include dephosphorylating the ADC, reducing and/or denaturing the ADC, and enzymatically digesting the ADC. Enzymatic digestion of the ADC may be accomplished by contacting the antibody with a proteolytic enzyme, for example, trypsin, chymotrypsin, papain, pepsin, LysN, LysC, AspN, GluC, ArgC, PNGaseF, or combinations of such enzymes. In these methods, the digestion may separate the drug from the antibody of the ADC. Alternatively, the drug may be separated after the digestion of the antibody. In these methods, the ADC may be contacted with a reagent that specifically separates the drug from the ADC.

The analysis of the digested antibody-drug conjugate peptide mixture may be conducted by LC-MS/MS, and such analysis may include detecting one peptide fragment from the digested ADC. The analysis also includes detecting the drug moiety within the digested antibody-drug conjugate peptide mixture. The drug may be detected as a peptide-linker-drug complex.

These analysis methods may determine the total antibody concentration of the antibody-drug conjugate, antibody-conjugated drug concentration of the ADC, and/or the average drug-to-antibody ratio (JAR) of the ADC.

In these analytical methods, the antibody portion of the ADC may be an antibody fragment, or an antibody variant that includes amino acid residues that have been substituted with cysteine residues. These antibodies, fragments or variants may be human or humanized antibodies.

An exemplary multiplexed analytical method of this disclosure is capable of quantifying both antibody-conjugated drug and total antibody concentrations of an antibody-drug conjugate present in a biological sample, such as blood, serum, plasma, tissue, or cells, by contacting the biological sample with an affinity capture media to form an ADC-affinity capture media complex. The complex is washed to reduce non-antibody proteins in contact with the ADC. The ADC-affinity capture media complex is then washed with a composition that reduces the antibody to form a denatured antibody. The antibody is also enzymatically digested to form a digested ADC peptide mixture in a single analysis sample. This single analysis sample is then analyzed by LC-MS/MS to detect at least one signature peptide of the antibody and a drug moiety. At least one characteristic of the ADC may then be determined from the LC-MS/MS analysis, including for example, total antibody concentration of the ADC, antibody-conjugated drug concentration of the ADC, and average drug-to-antibody ratio (DAR) of the ADC.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

BRIEF DESCRIPTION OF DRAWINGS

FIG. 3 shows a plot of the internal standard peak area for individual samples digested and either quenched by acid addition, or not quenched.

4

Figure 5A:
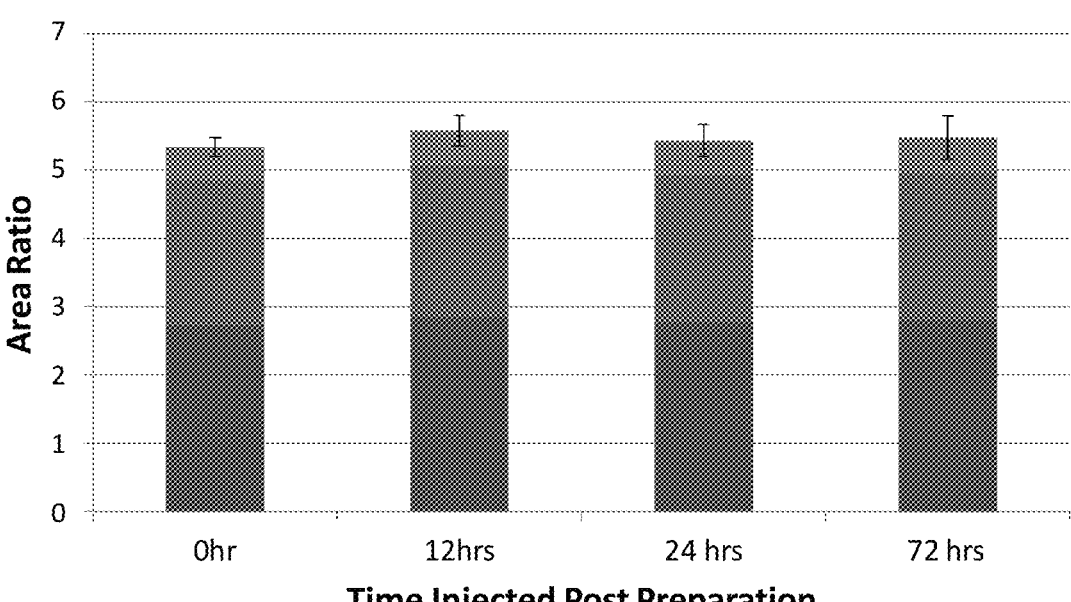

FIG. 5A shows a plot of the peak area of a peptide from the antibody digest, used for quantifying total antibody, after preparation and addition of methanol in acidic solution.

Figure 5B:
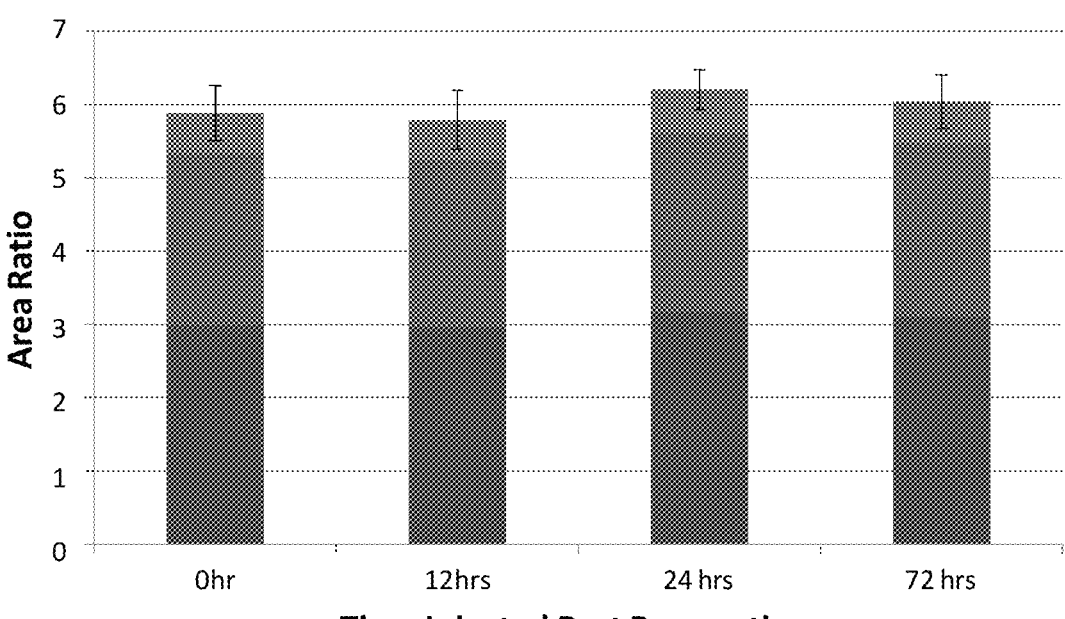

FIG. 5B shows a plot of the peak area of the peptide after preparation and addition of methanol in basic solution.

DESCRIPTION OF EMBODIMENTS

This disclosure is drawn to single measurement methods to detect and quantify antibody and drug components of antibody drug conjugates (ADCs) that robustly measure total antibody and antibody-conjugated drug quantity from a single sample preparation thereby providing drug to antibody ratio (DAR) calculation and significant time and resource savings.

Unless defined otherwise, technical and scientific terms used herein have the same meaning as commonly understood by one of ordinary skill in the art to which this invention belongs, and are consistent with: Singleton et al, (1994) "Dictionary of Microbiology and Molecular Biology", 2nd Ed., J. Wiley & Sons, New York, N.Y.; and Janeway, et al (2001) "Immunobiology", 5th Ed., Garland Publishing, New York. When trade names are used herein, the trade name product formulation, the generic drug, and the active pharmaceutical ingredient(s) of the trade name product are also included.

Definitions

The term "biological sample" is any component derived or separated from an animal and includes blood, plasma, serum, cells, urine, cerebrospinal fluid (CSF), milk, bronchial lavage, bone marrow, amniotic fluid, saliva, bile, vitreous, tears, or tissue.

The term "digestive enzyme" is an enzyme capable of cleaving or hydrolyzing peptides or proteins into fragments in either a specific or generic, random manner. A digestive enzyme can form a digested antibody sample from an antibody where the antibody is a component of a biological sample. Digestive enzymes include proteases such as trypsin, papain, pepsin, endoproteinase LysC, endoproteinase ArgC, staph aureus V8, chymotrypsin, Asp-N, Asn-C, PNGaseF, endoproteinase GluC, and LysN.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); WO 93/16185; U.S. Pat. Nos. 5,571,894; 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific (EP 404097; WO 1993/01161; Hudson et al. (2003) Nat. Med. 9:129-134; Hollinger et al. (1993) Proc. Natl. Acad. Sci. USA 90: 6444-6448). Triabodies and tetrabodies are also described in Hudson et al. (2003) Nat. Med. 9:129-134.

Single-domain antibodies are antibody fragments comprising all or a portion of the heavy chain variable domain or all or a portion of the light chain variable domain of an antibody. In certain embodiments, a single-domain antibody is a human single-domain antibody (U.S. Pat. No. 6,248, 516).

Antibody fragments can be made by various techniques, including but not limited to proteolytic digestion of an intact antibody as well as production by recombinant host cells (e.g. E. coli or phage), as described herein.

The term "chimeric" antibody refers to an antibody in which a portion of the heavy and/or light chain is derived from a particular source or species, while the remainder of the heavy and/or light chain is derived from a different source or species The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to constant domain residues other than hypervariable region (HVR) residues. The FR of a constant domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework region of an antibody which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "chimeric" antibody comprises a non-human variable region (e.g., a variable region derived from a mouse, rat, hamster, rabbit, or non-human primate, such as a monkey) and a human constant region (U.S. Pat. No. 4,816,567; Morrison et al. (1984) Proc. Natl. Acad. Sci. USA, 81:6851-6855). In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337; 7,527,791; 6,982,321; 7,087,409; Kashmiri et al. (2005) Methods 36:25-34 (describing SDR (a-CDR) grafting); Padlan, (1991) Mol. Immunol. 28:489-498 (describing "resurfacing"); Dall'Acqua et al. (2005) Methods 36:43-60 (describing "FR shuffling"); and Osbourn et al, (2005) Methods 36:61-68; Klimka et al. (2000) Br. J. Cancer 83:252-260 (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (Carter et al. (1992) Proc. Natl. Acad. Sci. USA, 89:4285; Presta et al. (1993) J. Immunol., 151:2623); human mature (somatically mutated) framework regions or human germline framework regions (Almagro and Fransson, (2008) Front. Biosci. 13:1619-1633); and framework regions derived from screening FR libraries (see, e.g., Baca et al. (1997) J. Biol. Chem. 272:10678-10684; and Rosok et al. (1996) J. Biol. Chem. 271:22611-22618).

Human antibodies can be produced using various techniques known in the art. Human antibodies are described generally in van Dijk and van de Winkel, (2001) Curr. Opin. Pharmacol. 5: 368-74; Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., (1991) J. Immunol., 147: 86) Human antibodies generated via human B-cell hybridoma technology are also described in Li et al., Proc. Natl. Acad. Sci. USA, 103:3557-3502 (2006). Additional methods include those described, for example, in U.S. Pat. No. 7,189,826 (describing production of monoclonal human IgM antibodies from hybridoma cell lines); Ni, (2006) Xiandai Mianyixue, 26(4):265-268 (describing human-human hybridomas). Human hybridoma technology (Trioma technology) is also described in Vollmers and Brandlein, (2005) Histology and Histopathology, 20(3):927-937 and Vollmers and Brandlein, (2005) Methods and Findings in Experimental and Clinical Pharmacology, 27(3):185-91.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al. (1992) J. Mol. Biol. 222: 581-597; Marks and Bradbury, in Methods in Molecular Biology 248:161-175 (Lo, ed., Human Press, Totowa, N.J., 2003); Sidhu et al. (2004) J. Mol. Biol. 338(2): 299-310; Lee et al. (2004) J. Mol. Biol. 340(5): 1073-1093; Fellouse, (2004) Proc. Natl.

Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., EMBO J, 12: 725-734 (1993). Finally, naive libraries can also be made synthetically by cloning un-rearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Human antibody phage libraries are described in U.S. Pat. No. 5,750,373; US 2005/0079574; US 2005/0119455; US 2005/0266000; US 2007/0117126; US 2007/0160598; US 2007/0237764; US 2007/0292936; US 2009/0002360. Antibodies or antibody fragments isolated from human antibody libraries are considered human antibodies or human antibody fragments herein.

An antibody may be a multispecific antibody, e.g. a bispecific antibody. Multispecific antibodies are monoclonal antibodies that have binding specificities for at least two different sites. One of the binding specificities may be for one antigen while the other is for a second antigen. Alternatively, bispecific antibodies may bind to two different epitopes of the same antigen. Bispecific antibodies may also be used to localize cytotoxic agents to cells which express an antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (Gruber et al., J. Immunol., 152:5368 (1994)); and preparing trispecific antibodies (Tutt et al. (1991) J. Immunol. 147: 60).

Engineered antibodies with three or more functional antigen binding sites, including "Octopus antibodies," are also included herein (see, e.g. U.S. Patent Publication No. 2006/0025576).

The antibody or fragment herein also includes a "Dual Acting FAb" or "DAF" comprising an antigen binding site that binds to an antigen as well as another, different antigen (see, U.S. Patent Publication No. 2008/0069820, for example).

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Antibodies include fusion proteins comprising an antibody and a protein, drug moiety, label, or some other group. Fusion proteins may be made by recombinant techniques, conjugation, or peptide synthesis, to optimize properties such as pharmacokinetics. The human or humanized antibody of the invention may also be a fusion protein comprising an albumin-binding peptide (ABP) sequence (Dennis et al. (2002) "Albumin Binding As A General Strategy For Improving The Pharmacokinetics Of Proteins" J Biol. Chem. 277:35035-35043; WO 01/45746). Antibodies of the invention include fusion proteins with ABP sequences taught by: (i) Dennis et al (2002) J Biol. Chem. 277:35035-35043 at Tables III and IV, page 35038; (ii) US 2004/0001827 at [0076]; and (iii) WO 01/45746 at pages 12-13, all of which are incorporated herein by reference.

Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region (Wright et al. (1997) TIBTECH 15:26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function (US 2003/0157108; US 2004/0093621). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. (2004) Biotech. Bioeng. 87:614. Examples of cell lines capable of producing defucosylated antibodies include Lec13 CHO cells deficient in protein fucosylation (Ripka et al. Arch. Biochem. Biophys. 249:533-545 (1986); US 2003/0157108, Presta, L; and WO 2004/056312, Adams et al., especially at Example 11), and knockout cell lines, such as alpha-1,6-fucosyltransferase gene, FUT8, knockout CHO cells (Yamane-Ohnuki et al (2004) Biotech. Bioeng. 87:614; Kanda, Y. et al. (2006) Biotechnol. Bioeng., 94(4):680-688; WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US Patent Pub. No. 2005/0123546 (Umana et al.). Antibody variants with at least one galactose residue in the oligosaccharide attached to the Fc region are also provided. Such antibody variants may have improved CDC function. Such antibody variants are described (WO 1997/30087; WO 1998/58964; WO 1999/22764).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on of in vitro assays to assess ADCC activity of a molecule of interest is described in U.S. Pat. No. 5,500,362; Hellstrom, I. et al. (1986) Proc. Nat'l Acad. Sci. USA 83:7059-7063); Hellstrom, I et al. (1985) Proc. Nat'l Acad. Sci. USA 82:1499-1502; U.S. Pat. No. 5,821,337; Bruggemann, M. et al. (1987) J. Exp. Med. 166:1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (Gazzano-Santoro et al. (1996), J. Immunol. Methods 202:163; Cragg, M. S. et al. (2003) Blood 101: 1045-1052; Cragg, M. S, and M. J. Glennie, (2004) Blood 103:2738-2743). FcRn binding and in vivo clearance/half-life determinations can also be performed using methods known in the art (Petkova, S. B. et al. (2006) Int'l. Immunol. 18(12):1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Additionally, antibody variants with improved or diminished binding to FcRs are described. (U.S. Pat. No. 6,737, 056; WO 2004/056312; Shields et al. (2001) J. Biol. Chem. 9(2): 6591-6604).

An antibody variant may comprise an Fc region with one or more amino acid substitutions which improve ADCC, e.g., substitutions at positions 298, 333, and/or 334 of the Fc region (EU numbering of residues).

Alterations may be made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. (2000) J. Immunol. 164: 4178-4184.

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

Cysteine Engineered Antibody Variants

It is desirable to create cysteine engineered antibodies (e.g., a THIOMAB™), in which one or more residues of an antibody are substituted with cysteine residue(s). The substituted residues may occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an antibody-drug conjugate (ADC), also referred to as an immunoconjugate. Examples of such THIOMABs include cysteine engineered antibodies in which any one or more of the following residues may be substituted with cysteine: V205 (Kabat numbering) of the light chain; A118 (EU numbering) of the heavy chain; and S400 (EU numbering) of the heavy chain Fc region, and S121, and K149 of the light chain. Exemplary methods of making cysteine engineered antibodies include, but are not limited to, the methods described, e.g., in U.S. Pat. No. 7,521,541 which is incorporated herein by reference in its entirety.

Thus, the methods of this disclosure may be applied to antibody-drug conjugates comprising cysteine engineered antibodies wherein one or more amino acids of a wild-type or parent antibody are replaced with a cysteine amino acid (THIOMAB™). Any form of antibody may be so engineered, i.e. mutated. For example, a parent Fab antibody fragment may be engineered to form a cysteine engineered Fab. Similarly, a parent monoclonal antibody may be engineered to form a THIOMAB™. It should be noted that a single site mutation yields a single engineered cysteine residue in a Fab antibody fragment, while a single site mutation yields two engineered cysteine residues in a full length THIOMAB™, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

Cysteine amino acids may be engineered at reactive sites in the heavy chain (HC) or light chain (LC) of an antibody and which do not form intrachain or intermolecular disulfide linkages (Junutula, et al., 2008b Nature Biotech., 26(8):925-932; Dornan et al (2009) Blood 114(13):2721-2729; U.S. Pat. Nos. 7,521,541; 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the linker-drug intermediates of the present invention which have thiol-reactive, electrophilic pyridyl disulfide groups to form ADC with cysteine engineered antibodies (THIOMAB™) and the drug (D) moiety. The location of the drug moiety can thus be designed, controlled, and known. The drug loading can be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A drug loading near 2 can be achieved and near homogeneity of the conjugation product ADC.

Cysteine engineered antibodies preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

Cysteine engineered antibodies are prepared for conjugation with linker-drug intermediates by reduction and reoxidation of intrachain disulfide groups.

Cysteine engineered antibodies which may form the antibody-drug conjugates for use in the methods of this disclosure include cysteine engineered antibodies useful in the treatment of cancer including, but not limited to, antibodies against cell surface receptors and tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed below. For convenience, information relating to these antigens, all of which are known in the art, is listed below and includes names, alternative names, Genbank accession numbers and primary reference(s), following nucleic acid and protein sequence identification conventions of the National Center for Bio-technology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens:

(1) BMPR1B (bone morphogenetic protein receptor-type IB, Genbank accession no. NM_001203) ten Dijke, P., et al Science 264 (5155):101-104 (1994), Oncogene 14 (11):1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377(Page 349-350); WO200230268 (claim 27; Page 376); WO200148204 (Example; FIG. 4) NP_001194 bone morphogenetic protein receptor, type IB/pid=NP_001194.1—Cross-references: MIM: 603248; NP_001194.1; AY065994

Figure 3:
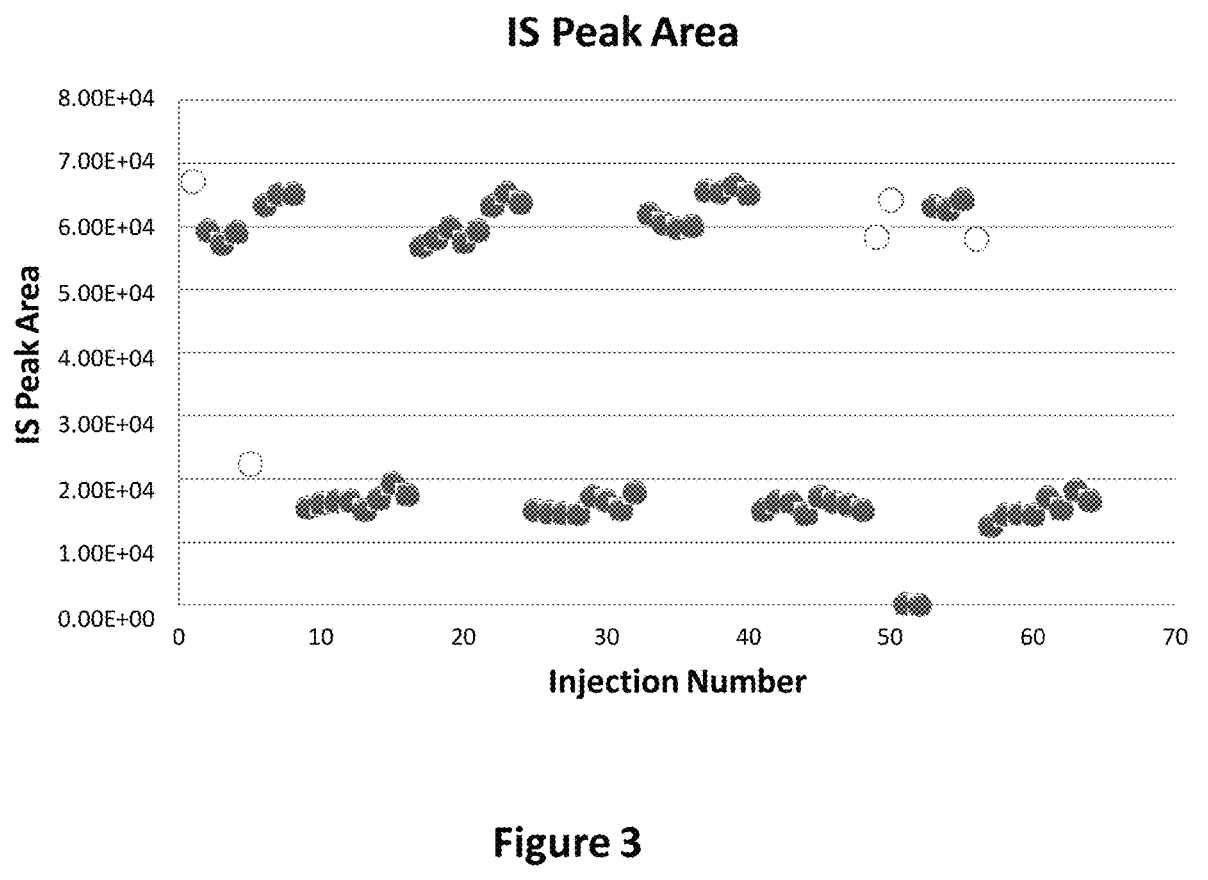

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150); NP_003477 solute carrier family 7 (cationic amino acid transporter, y+system), member

16

5/pid=NP_003477.3 —Homo sapiens Cross-references: MIM:600182; NP_003477.3; NM_015923; NM_003486_1

Figure 1:
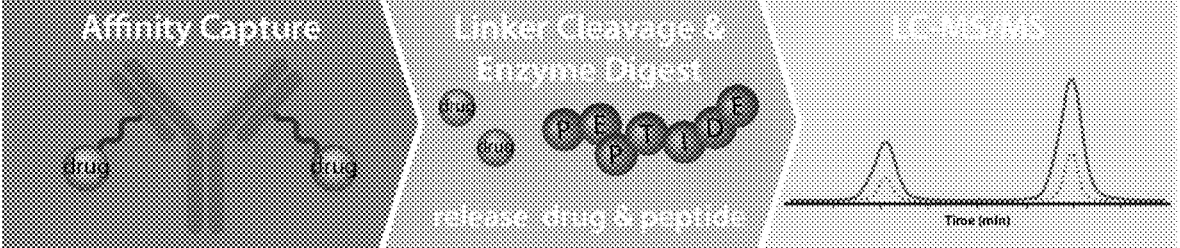
FIG. 1, shows a cartoon of an ADC analysis method including affinity capture of an ADC from a sample, enzymatic digestion and drug cleavage from the ADC, and simultaneous LC-MS/MS analysis of the drug and peptide fragments present in the single treated sample.
Figure 2A:
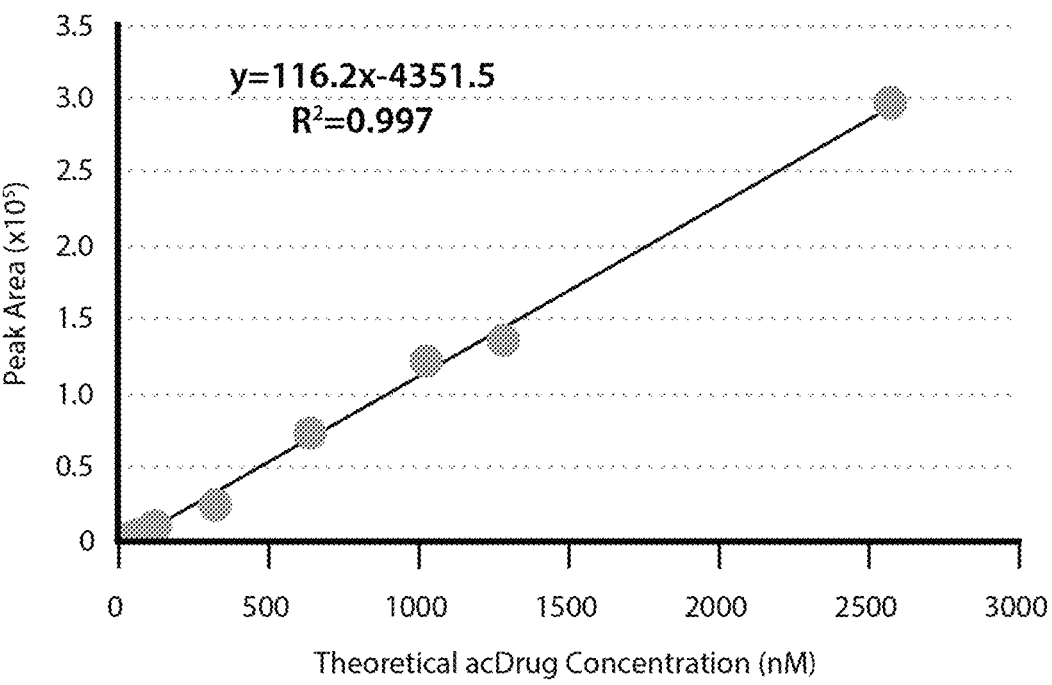
FIG. 2A shows a plot of drug (the pyrrolobenzodiazepine (PBD) SG2057) peak area versus drug concentration showing a linear, concentration-dependent reduction and release of drug.

(3) STEAP1 (six transmembrane epithelial antigen of prostate, Genbank accession no. NM_012449) Cancer Res. 61 (15), 5857-5860 (2001), Hubert, R. S., et al (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate. Cross-references: MIM:604415; NP_036581.1; NM_012449_1

(4) 0772P (CA125, MUC16, Genbank accession no. AF361486) J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); U.S. Pat. No. 798,959. Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57); Cross-references: MINI:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22): 19665-19672 (2002), Genomics 62 (2):281-284 (1999), Feild, J. A., et al (1999) Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140); Cross-references: MIM:604217; NP_006415.1; NM_006424_1

(7) Sema 5b (F1110372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11); Accession: Q9P283; EMBL; AB040878; BAA95969.1. Genew; HGNC:10737;

(8) PSCA hlg (2700050C12Rik, C530008016Rik, RIKEN cDNA 2700050C12, RIKEN cDNA 2700050C12 gene, Genbank accession no. AY358628); Ross et al (2002) Cancer Res. 62:2546-2553; US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein F1120315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6); Cross-references: LocusID:54894; NP_060233.2; NM_017763_1

Figure 4A:
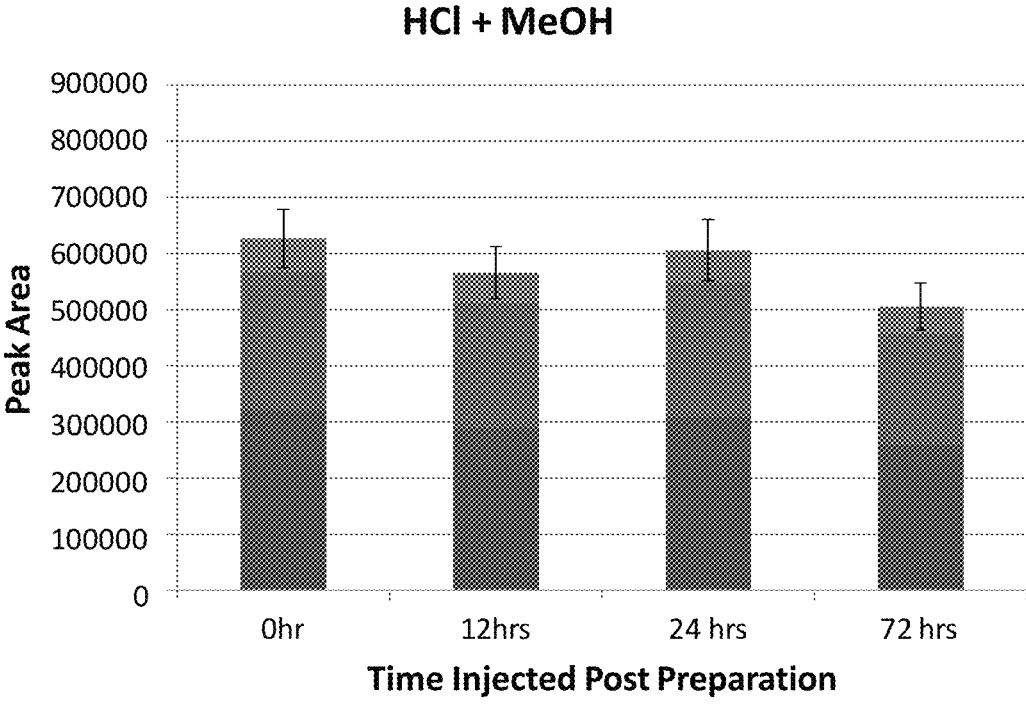
FIG. 4A shows a plot of the peak area of analyzed drug after preparation and addition of methanol in acidic solution.
Figure 4B:
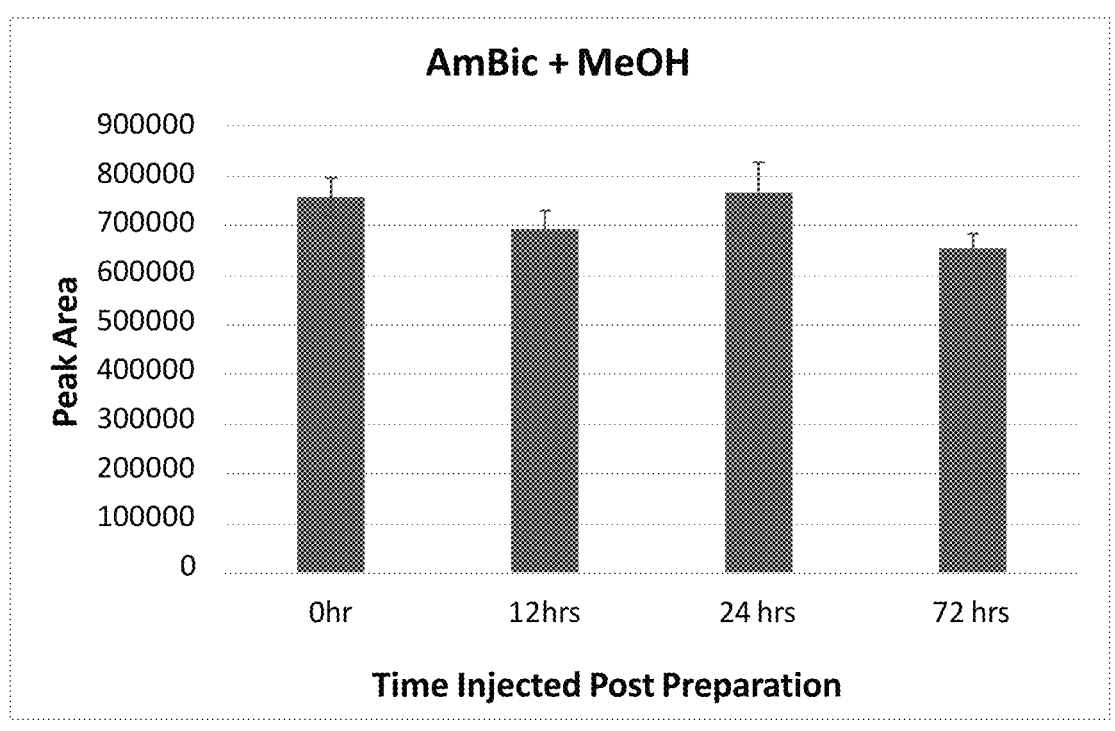
FIG. 4B shows a plot of the peak area of the analyzed drug after preparation and addition of methanol in basic solution.

(11) STEAP2 (HGNC 8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636). Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003));

US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D); Cross-references: MIM: 606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212). Ciccodicola, A., et al EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004). Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (claim 9); WO2004045520 (Example 4); WO9102536 (FIGS. 9.1-9.9); WO2004020595 (claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674). Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130). Genome Res. 13 (10):2265-2270 (2003), Immunogenetics 54 (2):87-95 (2002), Blood 99 (8): 2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (claim 2); WO2003077836; WO200138490 (claim 5; FIG. 18D-1-18D-2); WO2003097803 (claim 12); WO2003089624 (claim 25); Cross-references: MIM:606509; NP_110391.2; NM_030764_1

(17) HER2 (ErbB2, Genbank accession no. M11730) Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869, 445 (claim 3; Col 31-38); WO9630514 (claim 2; Page 56-61); EP1439393 (claim 7); WO2004043361 (claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2); Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (claim 1); WO200264798 (claim 33; Page 85-87); JP05003790 (FIG. 6-8); WO9946284 (FIG. 9); Cross-references: MIM:179780; AAH17023.1; BC017023_1

(20) IL20Rα0 (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59); Accession: Q9UHF4; Q6UWA9; Q96SH8; EMBL; AF184971; AAF01320.1.

(21) Brevican (BCAN, BEHAB, Genbank accession no. AF229053). Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000));

WO2003042661 (claim 12); WO200053216 (claim 1; Page 41); WO2004065576 (claim 1); WO2004020583 (claim 9); WO2003004529 (Page 128-132); WO200053216 (claim 1; Page 42); Cross-references: MIM:600997; NP_004433.2; NM_004442_1

(23) ASLG659 (B7h, Genbank accession no. AX092328). US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIG. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318;

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B); Accession: 043653; EMBL; AF043498; AAC39607.1.

(25) GEDA (Genbank accession No. AY260763); AAP14954 lipoma HMGIC fusion-partner-like protein/pid=AAP14954.1 —Homo sapiens Species: Homo sapiens (human) WO2003054152 (claim 20); WO2003000842 (claim 1); WO2003023013 (Example 3, Claim 20); US2003194704 (claim 45); Cross-references: GI:30102449; AAP14954.1; AY260763_1.

(26) BAFF-R (B cell-activating factor receptor, BLyS receptor 3, BR3, Genbank accession No. AF116456); BAFF receptor/pid=NP_443177.1 —Homo sapiens. Thompson, J. S., et al Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3); Cross-references: MIM:606269; NP_443177.1; NM_052945_1; AF132600.

(27) CD22 (B-cell receptor CD22-B isoform, BL-CAM, Lyb-8, Lyb8, SIGLEC-2, FLJ22814, Genbank accession No. AK026467); Wilson et al (1991) J. Exp. Med. 173:137-146; WO2003072036 (claim 1; FIG. 1); Cross-references: MIM:107266; NP_001762.1; NM_001771_1.

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10); WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5): 1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1); WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession No. NP_002111.1) Tonnelle et al (1985) EMBO J. 4(11):2839-2847; Jonsson et al (1989) Immunogenetics 29(6):411-413; Beck et al (1992) J. Mol. Biol. 228: 433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2); Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1); WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR)

family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1); US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1); WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human:AF343662, AF343663, AF343664, AF343665, AF369794, AF397453, AK090423, AK090475, AL834187, AY358085; Mouse:AK089756, AY158090, AY506558; NP_112571; WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84;

(37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. USA. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al (2003) Oncogene 22 (18): 2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E; Ly67, RIG-E, SCA-2, TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;

(41) TMEM46 (shisa homolog 2 (Xenopus laevis); SHISA2); NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1); NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KISS1 receptor; KISS1R; GPR54; HOT7T175; AXOR12); NP_115940.2; NM_032551.4; Navenot, J. M. et al (2009) Mol. Pharmacol. 75 (6): 1300-1306; Hata, K. et al (2009) Anticancer Res. 29 (2):617-623;

(48) ASPHD1 (aspartate beta-hydroxylase domain containing 1; LOC253982); NP_859069.2; NM_181718.3; Gerhard, D. S. et al (2004) Genome Res. 14 (10B): 2121-2127;

(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A; GPCR41; FLJ11856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) J. Clin. Invest. 75:756-56; Andrews et al., (1986) Blood 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15): 14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

Antibody Derivatives

An antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Conjugates of an antibody and nonproteinaceous moiety may be formed by selectively heating by exposure to radiation. The nonproteinaceous moiety of such conjugate may be a carbon nanotube (Kam et al. (2005) Proc. Natl. Acad. Sci. USA 102:11600-11605). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, (1987) J. Mol. Biol. 196:901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro and Fransson, (2008) Front. Biosci. 13:1619-1633). Unless otherwise indicated, HVR residues and other residues in the variable domain (e.g., FR residues) are numbered herein according to Kabat et al., supra.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al. (2007) J. Chromatogr. B 848:79-87.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See for example, Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (Portolano et al. (1993) J. Immunol. 150:880-887; Clarkson et al. (1991) Nature 352:624-628).

"Tumor-associated antigens" (TAA) are known in the art, and can prepared for use in generating human or humanized antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. Examples of TAA include, but are not limited to, those described in U.S. Pat. Nos. 8,679,767 and 8,541,178, which are expressly incorporated herein by reference, in their entirety.

The antibody components of the ADCs useful in the methods of this disclosure may be produced using recombinant methods and compositions, e.g., as described in U.S. Pat. No. 4,816,567. Isolated nucleic acids encoding such antibodies described herein are provided. Such nucleic acids may encode an amino acid sequence comprising the VL and/or an amino acid sequence comprising the VH of the antibody (e.g., the light and/or heavy chains of the antibody). One or more vectors (e.g., expression vectors) comprising such nucleic acid are also provided. A host cell comprising such nucleic acid is also provided. A host cell may comprise (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. The host cell may be eukaryotic, e.g. a Chinese Hamster Ovary (CHO) cell or lymphoid cell (e.g., Y0, NS0, Sp20 cell). Thus, methods of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells. For example, antibodies may be produced in bacteria, in particular when glycosylation and Fc effector function are not needed. For expression of antibody fragments and polypeptides in bacteria, see, e.g., U.S. Pat. Nos. 5,648,237; 5,789,199; 5,840,523; Charlton, Methods in Molecular Biology, Vol. 248 (B. K. C. Lo, ed., Humana Press, Totowa, N.J., (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (Gerngross, (2004) Nat. Biotech. 22:1409-1414; Li et al. (2006) Nat. Biotech. 24:210-215).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (U.S. Pat. Nos. 5,959,177; 6,040,498; 6,420,548; 7,125,978; 6,417, 429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. (1977, J. Gen Virol. 36:59); baby hamster kidney cells (BHK); mouse sertoli cells (TM4 cells as described, e.g., in Mather, (1980) Biol. Reprod. 23:243-251); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al. (1982) Annals N.Y. Acad. Sci. 383:44-68; MRC 5 cells; and FS4 cells. Other useful mammalian host cell lines include Chinese hamster ovary (CHO) cells, including DHFR-CHO cells (Urlaub et al. (1980) Proc. Natl. Acad. Sci. USA 77:4216); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

The antibody components of an ADC may be identified, screened for, or characterized for their physical/chemical properties and/or biological activities by various assays known in the art. An antibody may be tested for its antigen binding activity, e.g., by known methods such as ELISA, Western blot, etc. Competition assays may also be used to identify an antibody that competes with another known antibody for binding to antigen. In certain embodiments, such a competing antibody binds to the same epitope (e.g., a linear or a conformational epitope) that is bound by the known antibody. Detailed exemplary methods for mapping an epitope to which an antibody binds are provided in Morris (1996) "Epitope Mapping Protocols," in Methods in Molecular Biology, Vol. 66 (Humana Press, Totowa, N.J.).

Exemplary antibodies forming the ADC may include, but are not limited to, trastuzumab, ocrelizumab, pertuzumab, anti-PDLL, anti-neuropilin-1, anti-MUC16, rituximab, anti-mesothelin, anti-LY6E, anti-STEAP1, anti-FcRH5, anti-CD22, anti-B7H4, anti-LGR5, anti-CD79b, and anti-*Napi*2b.

Drug moieties which form the drug component of the ADC may be covalently attached to antibodies through a linker unit to form antibody-drug conjugates for targeted therapeutic effects. An exemplary embodiment of an anti-body-drug conjugate (ADC) compound comprises an antibody (Ab) which targets, e.g., a tumor cell, cytotoxic or cytostatic drug moiety (D), and a linker moiety (L) that attaches Ab to D. The antibody is attached through the one or more amino acid residues, such as lysine and cysteine, by the linker moiety (L) to D; the composition having the Formula: Ab-(L-D)p, where p is 1 to about 20, or from about 2 to about 5. The number of drug moieties which may be conjugated via a reactive linker moiety to an antibody molecule may be limited by the number of cysteine residues, including free cysteine residues present in the antibody or which may be introduced by methods described herein, or native cysteines that form the interchain disulfide bonds of the antibody.

The drug moiety (D) of an antibody-drug conjugate (ADC) may include any therapeutic compound, moiety or group, especially a group that has a cytotoxic or cytostatic effect. Exemplary drug moieties may impart such cytotoxic and cytostatic effects by mechanisms including but not limited to tubulin binding, DNA binding or intercalation, and inhibition of RNA polymerase, protein synthesis, and topoisomerase. Some cytotoxic drugs tend to be inactive or less active when conjugated to large antibodies or protein receptor ligands. Exemplary drug moieties include, but are not limited to, a maytansinoid, dolastatin, auristatin, cali-cheamicin, pyrrolobenzodiazepine (PBD), PNU-159682, anthracycline, duocarmycin, vinca alkaloid, taxane, trichot-hecene, CC1065, duocarmycin, camptothecin, elinafide, an antibiotic including a rifamycin or rifamycin-analog, and stereoisomers, isosteres, analogs or derivatives thereof, including derivatives of these drugs that have cytotoxic activity.

Antibody-drug conjugates (ADC) are targeted anti-cancer therapeutics designed to reduce nonspecific toxicities and increase efficacy relative to conventional small molecule and antibody cancer chemotherapy. They employ the powerful targeting ability of monoclonal antibodies to specifically deliver highly potent, conjugated small molecule therapeutics to a cancer cell. To evaluate properties such as efficacy, stability, homology, pharmacokinetics and toxicity of these ADCs, it is useful to be able to characterize and quantify the antibody component and drug moiety simultaneously from solution, plasma, urine, and other biological samples, via a single sample analytical analysis. Methods to detect and screen antibody-drug conjugates by Immunoaffinity membrane (IAM) capture and mass spectrometry have been disclosed (US 2005/0232929), including bead-based affinity capture methods (US 2009/0286258).

Methods of Simultaneous Quantification of Antibody and Drug Moieties in Single Sample Assays This disclosure provides reproducible, efficient and economic LC-MS/MS-based methods for simultaneous quantification of antibody and drug components of ADC therapeutic constructs. FIG. 1 shows a cartoon of the work flow in an ADC sample assay of this disclosure, including the optional affinity capture of an ADC from a sample, enzymatic digestion and drug cleavage release from the ADC, and subsequent simultaneous analysis of the drug and peptide fragments present in the single treated sample by LC-MS/MS.

In these methods, ADC samples may be treated to reduce, denature, and digest the protein component of the sample to produce a digested antibody-drug conjugate peptide mixture in a single analysis sample. The single analysis sample comprising both the drug and the digested antibody components is then analyzed by liquid chromatography—tandem mass spectrometry (LC-MS/MS) to detect and quantify both the drug and antibody component of the ADC.

Depending upon the identity of the linker component of the ADC and the chemical treatment applied to reduce, denature, and/or digest the protein component of the sample, the drug moiety of the ADC may be cleaved from the antibody/peptide component of the ADC and may therefore be detected and quantified as an unconjugated drug component in the LC-MS/MS analysis.

Alternatively or additionally, the drug moiety component of the ADC may remain linked to the antibody/peptide component of the ADC following reduction and denaturation of the ADC, and may therefore be detected and quantified as a peptide-bound drug component in the LC-MS/MS analysis.

The LC-MS/MS analysis of the single analysis sample comprising both the drug and the antibody or antibody components, may be used to determine the total antibody concentration of the antibody-drug conjugate, the antibody-conjugated drug concentration of the ADC, and calculate the average drug-to-antibody ratio (DAR) of the ADC, and combinations of these characteristics of the ADC.

The sample containing the ADC for analysis/quantification may be subjected to reduction, denaturation, and/or digestion without any preliminary sample clean up or enrichment (i.e., "direct digestion" of the sample). Alternatively or additionally, the sample containing the ADC may be enriched or concentrated for further analysis. Such concentration of low-abundance peptides or drugs may include enrichment techniques such as size exclusion chromatography, dialysis, selective precipitation, differential centrifugation, filtration, gel electrophoresis, liquid chromatography, reversed-phase chromatography, immunoprecipitation, SpinTrap™ purification columns including protein A and protein G, NHS and streptavidin iron or phosphorus or immobilized antibodies or lectin, paramagnetic beads, immuno-depletion, fractionation, solid phase extraction, phosphopeptide enrichment, polyacrylamide gel electrophoresis, desalting, and the like.

The ADC presented for analysis may also be present in a solution or suspension, such as a pharmaceutical composition formulated for administration to an animal or human, or in cell culture or supernatant that may be present in a production step of the ADC, or in a biological sample obtained from an animal or a human. Thus, the ADC may be present in a matrix selected from a buffer, whole blood, serum, plasma, cerebrospinal fluid, saliva, urine, lymph, bile, feces, sweat, vitreous, tears, and tissue. Biological samples that are frequently presented for analysis of various safety, efficacy and pharmacokinetic/biodistribution parameters of ADCs include human, cynomolgus monkey, rat, and mouse plasma and tissue samples, as well as biological samples from other non-human species.

When presented as part of such biological samples, the ADC may be contacted with an affinity capture media. Affinity capture is a widely used method to enrich/isolate intact proteins, to identify binding partners and protein complexes, or to investigate post-translational modifications. The protein or protein complexes may be separated by non-specific means (e.g., gel electrophoresis, Protein A or G media, type 1 antineuronal nuclear autoantibody (ANNA-1, also known as "anti-Hu"), or specific means (e.g., extracellular domain (ECD) antibodies, or anti-idotypic antibodies). The ADC may then be eluted from the affinity capture media as a means of sample cleanup prior to reduction, denaturation, and/or digestion, and subsequent LC-MS/MS analysis.

Alternatively or additionally, the ADC sample is analyzed with an affinity capture by bead- or resin-supported Protein A/G, followed by on-bead dephosphorylation, reduction, denaturation, and/or digestion, prior to elution of an enriched digested antibody sample from the affinity capture media, and LC-MS/MS analysis. Methods to capture, wash and elute antibody-drug conjugates by Immunoaffinity membrane (IAM) capture and mass spectrometry have been disclosed (U.S. Patent Publication No. 2005/0232929), including bead-based affinity capture methods (U.S. Patent Publication No. 2009/0286258).

The ADC is reduced by contact with a composition that includes at least one reductant, for example dithiolthreitol (DTT), 2-mercaptoethanol, or tris(2-carboxyethyl)phosphine (TCEP). The ADC may also be denatured by contact with a composition that includes at least one denaturant, for example formamide, dimethylformamide, acetonitrile, SDS, urea, guanidine, sodium 3-((1-(furan-2-yl)undecyloxy)carbonylamino)propane-1-sulfonate (ProteaseMaxTm), and/or an acid labile surfactant(s) such as those containing a dioxolane or dioxane functional group, such as RapiGest™-SF-surfactant (as described in U.S. Pat. Nos. 7,229,539 and 8,580,533; which are incorporated herein by reference). The ADC may be simultaneously reduced and denatured by contact with a composition that includes at least one reductant and at least one denaturant. Such compositions may include additional solvents, buffers and/or pH modifying agents, such as acetonitrile, methanol, ethanol, HCl, ammonium bicarbonate, ammonium acetate, and/or formic acid, dephosphorylating agents including phosphatases such as calf intestinal alkaline phosphatase, bovine intestinal alkaline phosphatase, or lambda protein phosphatase.

The protein component of the sample may be digested with non-enzymatic proteolytic methods, such as acid hydrolysis in the presence of mineral acids or trifluoroacetic acid or formic acid, proteolysis with cyanogen bromide, or heat-induced proteolysis above 250° C. Alternatively or additionally, the sample may be digested with proteolytic enzyme such as trypsin, papain, pepsin, endoproteinase LysC, endoproteinase ArgC, staph aureus V8, chymotrypsin, Asp-N, Asn-C, PNGaseF, endoproteinase GluC, and LysN, or combinations of these enzymes.

The analysis sample comprising both the drug (or peptide-linker-drug) and the digested antibody components of the ADC is then applied as a single sample to a liquid chromatography support for separation and the effluent from the liquid chromatography is analyzed by mass spectrometry to establish the mass to charge ratio of at least one peptide fragment of the digested antibody, and the mass to charge ratio of the drug (or peptide-linker-drug) moiety of the ADC.

Digestion of the antibodies provides peptides in the single analysis sample which are unique to the antibody of the ADC. The proteolytic methods or enzyme(s) used to digest the antibody may be chosen to produce a unique peptide fragment for detection and quantitation by LC-MS/MS. One or more of the peptide fragments unique to the antibody of the ADC is detected and quantified by LC-MS/MS, thereby eliminating background or non-specific proteins or other contaminants that may be present in the single analysis sample applied to LC-MS/MS that do not form part of the ADC.

Each publication or patent cited herein is incorporated herein by reference in its entirety.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1: ADC Multiplexing Assay Design and Validation

In order to test and validate the multiplexing assays of this disclosure, cynomolgus monkey plasma from commercial source was used to fortify with an ADC (a disulfide linked to a pyrrolobenzodiazepine dimer, which is a cysteine engineered antibody prepared as described in U.S. Pat. No. 7,521,541) to provide standard calibration samples. Frozen plasma 15 samples obtained from cynomolgus monkeys that had previously been administered the ADC were also used for testing. Protein A magnetic beads (Pure Proteome) were washed in a buffer containing 0.1% by volume Tween® 20 (polyethylene glycol sorbitan monolaurate), 5.0% by volume Trizma® Hydrochloride (2-Amino-2-(hydroxymethyl)-1,3-propanediol) (1 M), 3.0% by volume sodium chloride (5 M), 0.2% by volume EDTA (0.5 M), 0.1% by weight Bovine Serum Albumin, and 91.7% by volume water, were washed 3 times. The protein A beads are then 20 incubated with the above wash buffer and thawed plasma samples for 2 hours at room temperature with constant shaking.

The beads were then washed 2 times in a buffer containing 5.0% by volume Trizma Hydrochloride (1 M), 3.0% by volume Sodium Chloride (5 M), 0.2% by volume EDTA (0.5 M), and 91.8% by volume water. The washed beads were then incubated in a 110 μl total reaction solution containing:

1) 75 μl denaturing solution (0.05% by weight RapiGest™ SF surfactant (Waters Corporation, Milford, MA), 37.5% by volume ammonium bicarbonate (50 mM), and 10% by volume acetonitrile);

2) 10 μl reducing solution (200 mM tris(2-carboxyethyl) phosphine (TCEP)); and 3) 25 μl stable labeled internal standard;

at neutral pH, for 1 hour at 60° C., with constant shaking.

The reduced samples/beads were then alkylated to prevent re-oxidation of the reduced cysteine residues, preventing re-form disulfide bonds from re-forming. The alkylation was conducted by incubation in a solution containing 25 μL of 200 mM iodoacetamide in 50 mM ammonium bicarbonate, pH 8, at room temperature, in the dark for 45 minutes.

The antibodies were then digested by adding 10 μL of digest solution (sequencing grade modified trypsin 250 ug/ml in 50 mM ammonium bicarbonate) to the reduced and alkylated samples, vortexing and incubating at 37° C. for 2 hours. The enzymatic digest was then quenched by adding 15 μl of 2M HCl, vortexing, and incubating at 37° C. for 30 min.

Protein in the sample is precipitated out by the addition of 4 volumes of an organic solvent which contains the drug internal standard.

The reduced and digested samples were then analyzed by LC-MS/MS (Shimadzu LC, AB SCIEX QTrap® 5500 mass spectrometers).

Table 2A provides a comparison of the data and FIG. 2A shows a plot of drug (SG2057) peak area versus drug concentration showing a linear, concentration-dependent reduction and release of drug, with an $r^2$ value of 0.997, and high percent accuracies within ±10%.

TABLE 2A

| acDrug (nM) | Measured acDrug (nM) | Accuracy (%) |
|---|---|---|
| 12.9 | 13.0 | 101 |
| 643.2 | 666.0 | 104 |
| 1029.1 | 1110.0 | 108 |
| 1286.4 | 1240.0 | 96.5 |
| 2572.8 | 2720.0 | 106 |

Figure 2B:
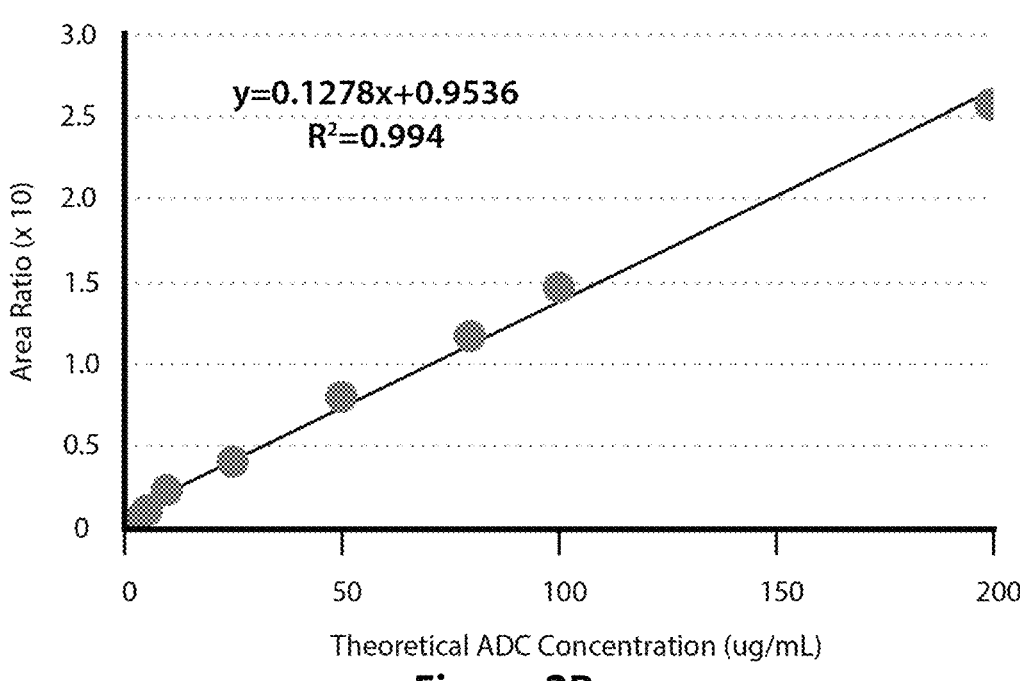
FIG. 2B shows a plot similar to FIG. 2A of total antibody peak area versus ADC concentration.

Table 2B provides a comparison of the data, and FIG. 2B shows a plot of total antibody peak area versus ADC concentration, which similarly shows a high $r^2$ value of 0.994, and high percent accuracies within ±20%. These data demonstrate the successful development of new, multiplexed assays for cysteine-engineered antibody drug conjugates (THIOMABs).

TABLE 2B

| total Ab (μg/mL) | Measured Total Ab (μg/mL) | % Accuracy |
|---|---|---|
| 1 | 0.997 | 99.7 |
| 50 | 53.5 | 107 |
| 80 | 79.1 | 98.8 |
| 100 | 99.9 | 99.9 |
| 200 | 175 | 87.4 |

Example 2: Acid Quench of Enzymatic Reaction

Frozen plasma samples containing an ADC were thawed and analyzed by LC-MS/MS as described in Example 1. As described in Example 1, a mild surfactant denaturant (RapiGest™ SF surfactant) was used to solubilize and unfold the proteins, thereby opening up the protein structure to expose proteolytic sites. At the digestion stage of preparing the samples for LC-MS/MS analysis, half of the samples processed did not have the enzymatic digestion quenched, while the other half of the processed samples had the enzymatic digestion quenched by the addition of acid (addition of HCl, as described in Example 1). The surfactant used was an acid-labile surfactant that undergoes hydrolysis in acidic conditions, to form inactive and non-interfering by-products, which do not suppress peptide ionization in subsequent MS analysis. The mild surfactant denaturant is not disruptive to protease activity, thereby reducing the amount of enzyme(s) required in the digestion step of the sample processing.

FIG. 3 shows a plot of the internal standard peak area for individual samples digested and either quenched by acid addition, or not quenched. These data demonstrate that the addition of acid to the enzymatic digestion quenches the enzymatic reaction, hydrolyzes the surfactant, and decreases ionization suppression caused by the surfactant, all the while not affecting sample stability. These data demonstrate that the surfactant does not affect the released drug, and suggest that this multiplexing assay can be performed without having the acid quench, or eliminating the use of the surfactant.

Example 3: Stability of Released Drug Component

To assess the stability of the drug in the reduced and digested samples, samples were prepared for LC-MS/MS analysis as described in Example 1 and preserved by the addition methanol (either in acidic solution containing HCl, or in basic solution containing ammonium bicarbonate). The samples were immediately analyzed, or saved and analyzed 12 hours, 24 hours, or 72 hours later. FIG. 4A shows a plot of the peak area of the analyzed drug after preparation and addition of methanol in acidic solution. Similarly, FIG. 4B shows a plot of the peak area of the analyzed drug after preparation and addition of methanol in basic solution. These data demonstrate that the released drug remains in solution containing methanol in either basic or acid solution. For use with sample preparation techniques that include an acid quench of the enzymatic digestion, FIG. 4A shows that the released drug remained stable and soluble up to 72 hours after sample preparation in presence of acid and organic protein precipitation.

Example 4: Stability of Digested Antibody Component

To assess the effects of acid quenching and methanol precipitation on quantitation of total antibody in the reduced and digested samples, samples were prepared for LC-MS/MS analysis as described in Example 1 and preserved by the addition methanol (either in acidic solution containing HCl, or in basic solution containing ammonium bicarbonate). The samples were immediately analyzed, or saved and analyzed 12 hours, 24 hours, or 72 hours later. FIG. 5A shows a plot of the peak area of a peptide from the antibody digest, used for quantifying total antibody, after preparation and addition of methanol in acidic solution. Similarly, FIG. 5B shows a plot of the peak area of the peptide after preparation and addition of methanol in basic solution. These data demonstrate that total antibody quantitation is also steady up to 72 hours after sample preparation consisting of acid quench and organic protein precipitation.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:

1. A method of quantifying both an antibody-conjugated drug concentration and a total antibody concentration of an antibody-drug conjugate (ADC) in a single analysis sample, the method comprising:

(a) contacting the ADC comprising an antibody, a drug moiety, and a linker moiety that attaches the antibody to the drug moiety, wherein the linker moiety of the ADC is a disulfide linker, and which is bound to an affinity capture media selected from the group consisting of: (1) bead- or resin-supported Protein A/G, and (2) target antigen-paramagnetic bead capture media, with (i) a reductant that reduces the antibody portion of the ADC to form a denatured antibody portion of the ADC, wherein the reductant is selected from the group consisting of dithiolthreitol (DTT), 2-mercaptoethanol, and tris(2-carboxyethyl)phosphine (TCEP), whereby the drug moiety is separated from the denatured antibody portion of the ADC; (ii) at least one denaturant selected from the group consisting of formamide, dimethylformamide, acetonitrile, SDS, urea, an acid labile surfactant, a decyl furanyl sulfonic acid salt, and guanidine HCl; and (iii) at least one chemical selected from the group consisting of methanol, ethanol, HCl, ammonium bicarbonate, Tris buffer, HEPES, ammonium acetate, and acetonitrile; whereby the antibody portion of the ADC is denatured;

(b) digesting the denatured antibody portion of the ADC bound to the affinity capture media to form a digested ADC peptide mixture from the single analysis sample with a proteolytic enzyme selected from the group consisting of trypsin, chymotrypsin, papain, pepsin, LysN, LysC, AspN, GluC, ArgC, and PNGaseF; and (c) eluting from the affinity capture media and analyzing the digested ADC peptide mixture by LC-MS/MS to detect at least one antibody signature peptide and the drug moiety in the single analysis sample.

2. The method of claim 1, wherein the ADC is suspended in a matrix selected from the group consisting of a buffer, whole blood, serum, plasma, cerebrospinal fluid, saliva, urine, lymph, bile, feces, sweat, vitreous, tears, and tissue, prior to the contacting step.

3. The method of claim 1, wherein the ADC is enriched by a technique selected from the group consisting of size exclusion chromatography, dialysis, selective precipitation, differential centrifugation, filtration, gel electrophoresis, liquid chromatography, reversed-phase chromatography, immunoprecipitation, spin columns including protein A and protein G, and desalting, prior to the contacting step.

4. The method of claim 1, further comprising washing ADC bound to the affinity capture media to reduce non-antibody proteins in contact with the ADC.

5. The method of claim 1, wherein the affinity capture media is bead- or resin-supported Protein A/G.

6. The method of claim 5, wherein the bead- or resin-supported Protein A/G is Protein A magnetic beads.

7. The method of claim 1, further comprising dephosphorylating the ADC bound to the affinity capture media.

8. The method of claim 1, wherein the reductant is tris(2-carboxyethyl)phosphine (TCEP).

9. The method of claim 1, wherein the denaturant is an acid labile surfactant.

10. The method of claim 1, wherein the total antibody concentration of the ADC is calculated from the analysis of the digested ADC peptide mixture.

11. The method of claim 1, wherein the antibody-conjugated drug concentration of the ADC is calculated from the analysis of the digested ADC peptide mixture.

12. The method of claim 1, wherein the average drug-to-antibody ratio (DAR) of the ADC is calculated from the analysis of the digested ADC peptide mixture.

13. The method of claim 1, wherein the drug moiety is selected from the group consisting of a maytansinoid, dolastatin, auristatin, calicheamicin, pyrrolobenzodiazepine (PBD), PNU-159682, anthracycline, duocarmycin, vinca alkaloid, taxane, trichothecene, CC1065, duocarmycin, camptothecin, and elinafide.

14. The method of claim 1, wherein the antibody portion of the ADC is an antibody fragment.

15. The method of claim 1, wherein the antibody portion of the ADC is a human or humanized antibody.

16. The method of claim 1, wherein the antibody portion of the ADC is an antibody which binds to one or more tumor-associated antigens or cell-surface receptors selected from the group consisting of (1)-(53):

(1) BMPRIB (bone morphogenetic protein receptor-type IB);
   (2) E16 (LAT1, SLC7A5);
   (3) STEAP1 (six transmembrane epithelial antigen of prostate);
   (4) MUC16 (0772P, CA125);
   (5) MPF (MPF, MSLN, SMR, megakaryocyte potentiating factor, mesothelin);
   (6) Napi2b (NAPI-3B, NPTIIb, SLC34A2, solute carrier family 34 (sodium phosphate), member 2, type II sodium-dependent phosphate transporter 3b);
   (7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
   (8) PSCA hlg (2700050C12Rik, C530008O16Rik, RIKEN cDNA 2700050C12, RIKEN cDNA 2700050C12 gene);
   (9) ETBR (Endothelin type B receptor);
   (10) MSG783 (RNF124, hypothetical protein FLJ20315);
   (11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
   (12) TrpM4 (BR22450, FLJ20041, TRPM4, TRPM4B, transient receptor potential cation channel, subfamily M, member 4);
   (13) CRIPTO (CR, CR1, CRGF, CRIPTO, TDGF1, teratocarcinoma-derived growth factor);
   (14) CD21 (CR2 (Complement receptor 2) or C3DR (C3d/Epstein Barr virus receptor) or Hs 73792);
   (15) CD79b (CD79B, CD79β, IGb (immunoglobulin-associated beta), B29);
   (16) FcRH2 (IFGP4, IRTA4, SPAP1A (SH2 domain containing phosphatase anchor protein 1a), SPAP1B, SPAP1C);
   (17) HER2;
   (18) NCA;
   (19) MDP;
   (20) IL20Rα;
   (21) Brevican;
   (22) EphB2R;
   (23) ASLG659;
   (24) PSCA;
   (25) GEDA;

(26) BAFF-R (B cell-activating factor receptor, BLyS receptor 3, BR3);

(27) CD22 (B-cell receptor CD22-B isoform);

(28) CD79a (CD79A, CD79a, immunoglobulin-associated alpha);

(29) CXCR5 (Burkitt's lymphoma receptor 1);

(30) HLA-DOB (Beta subunit of MHC class II molecule (Ia antigen));

(31) P2X5 (Purinergic receptor P2X ligand-gated ion channel 5);

(32) CD72 (B-cell differentiation antigen CD72, Lyb-2);

(33) LY64 (Lymphocyte antigen 64 (RP105), type I membrane protein of the leucine rich repeat (LRR) family);

(34) FcRH1 (Fc receptor-like protein 1);

(35) FcRH5 (IRTA2, Immunoglobulin superfamily receptor translocation associated 2);

(36) TENB2 (putative transmembrane proteoglycan);

(37) PMEL17 (silver homolog; SILV; D12S53E; PMEL17; SI; SIL);

(38) TMEFF1 (transmembrane protein with EGF-like and two follistatin-like domains 1; Tomoregulin-1);

(39) GDNF-Ral (GDNF family receptor alpha 1; GFRA1; GDNFR; GDNFRA; RETL1; TRNR1; RET1L; GDNFR-alpha1; GFR-ALPHA-1);

(40) Ly6E (lymphocyte antigen 6 complex, locus E; Ly67, RIG-E,SCA-2,TSA-1);

(41) TMEM46 (shisa homolog 2 (*Xenopus laevis*); SHISA2);

(42) Ly6G6D (lymphocyte antigen 6 complex, locus G6D; Ly6-D, MEGT1);

(43) LGR5 (leucine-rich repeat-containing G protein-coupled receptor 5; GPR49, GPR67);

(44) RET (ret proto-oncogene; MEN2A; HSCR1; MEN2B; MTC1; PTC; CDHF12; Hs.168114; RET51; RET-ELE1);

(45) LY6K (lymphocyte antigen 6 complex, locus K; LY6K; HSJ001348; FLJ35226);

(46) GPR19 (G protein-coupled receptor 19; Mm.4787);

(47) GPR54 (KISS1 receptor; KISS1R; GPR54; HOT7T175; AXOR12);

(48) ASPHD1 (aspartate beta-hydroxylase domain containing 1; LOC253982);

(49) Tyrosinase (TYR; OCA1A; OCALA; tyrosinase; SHEP3);

(50) TMEM118 (ring finger protein, transmembrane 2; RNFT2; FLJ14627);

(51) GPR172A (G protein-coupled receptor 172A; GPCR41; FLJ11856; D15Ertd747e);

(52) CD33; and

(53) CLL-1.

* * * * *